United States Patent [19]

Müller et al.

[11] 4,323,380

[45] Apr. 6, 1982

[54] RECTIFICATION OF GASEOUS MIXTURES

[75] Inventors: Karl-Heinz Müller, Geretsried; Wolfgang Förg, Icking, both of Fed. Rep. of Germany

[73] Assignee: Linde Aktiengesellschaft, Wiesbaden, Fed. Rep. of Germany

[21] Appl. No.: 175,817

[22] Filed: Aug. 6, 1980

[30] Foreign Application Priority Data

Aug. 10, 1979 [DE] Fed. Rep. of Germany ....... 2932561

[51] Int. Cl.$^3$ ............................................... F25J 3/06
[52] U.S. Cl. ........................................ 62/28; 62/38; 62/41; 62/26
[58] Field of Search ................. 62/41, 24, 27, 28, 26, 62/38, 39, 29

[56] References Cited

U.S. PATENT DOCUMENTS

| | | | |
|---|---|---|---|
| 2,559,132 | 7/1951 | Roberts | 62/41 |
| 2,600,494 | 6/1952 | Ferro, Jr. | 62/41 |
| 2,850,880 | 9/1958 | Jakob | 62/29 |
| 3,074,245 | 1/1963 | Becker | 62/41 |
| 3,163,511 | 12/1964 | Linde et al. | 62/41 |
| 4,061,481 | 12/1977 | Campbell et al. | 62/28 |
| 4,211,544 | 7/1980 | Springmann | 62/41 |

Primary Examiner—Norman Yudkoff
Attorney, Agent, or Firm—Millen & White

[57] ABSTRACT

In a process for the rectification of a raw gaseous mixture under superatmospheric pressure and containing at least three components, e.g. natural gas wherein the gaseous mixture is fractionated in a first rectifying column into a head product largely freed of at least one higher-boiling component and into a bottoms product largely freed of at least one lower-boiling component, the improvement which comprises compressing the liquid bottoms product of the first rectifying column; passing resultant compressed bottoms product in indirect heat exchange relationship with the gaseous mixture to at least partially vaporize said bottoms product; engine-expanding resultant vaporized compressed bottoms product to form a liquid which is then passed as reflux into a second rectifying column; and fractionating resultant expanded bottoms product in said second rectifying column to form a top product containing lower-boiling components and into a sump product containing higher-boiling components.

9 Claims, 1 Drawing Figure

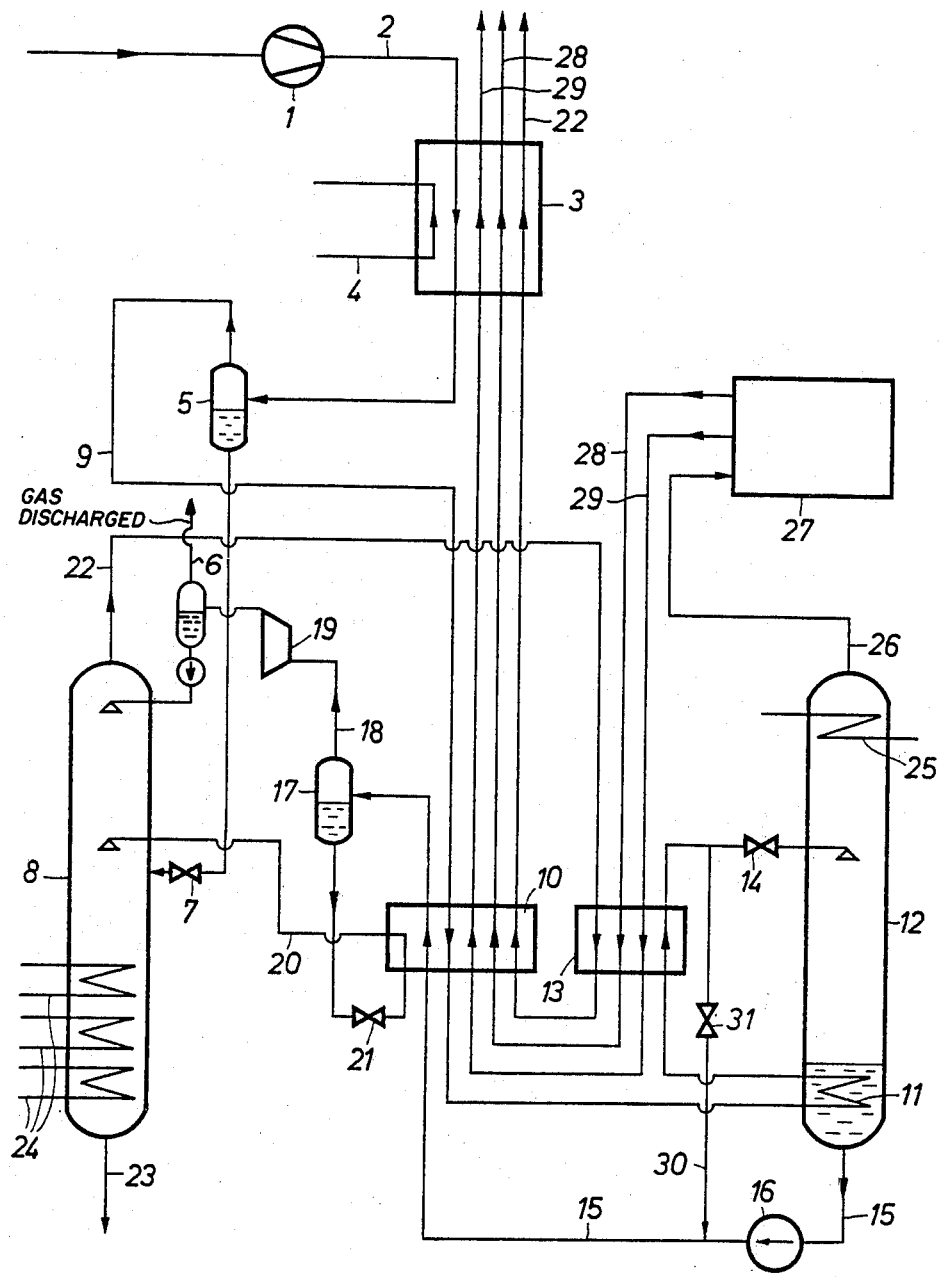

RECTIFICATION OF GASEOUS MIXTURES

BACKGROUND OF THE INVENTION

This invention relates to a process and apparatus for the fractionation of a gaseous mixture containing at least three components, said gaseous mixture being, for example, natural gas or the like.

DAS [German Published Application] No. 2,122,707 discloses a process wherein a gaseous mixture is fractionated in a first rectifying column into a head product largely freed of at least one higher-boiling component and into a bottoms product largely freed of at least one lower-boiling component. In this process, natural gas containing, in addition to methane, considerable amounts of nitrogen as well as carbon dioxide and higher hydrocarbons is initially fractionated in a first rectifying column into two fractions, the head product consisting essentially of nitrogen and methane, and the bottoms product containing not only a small amount of nitrogen, but also in addition to the main component methane, the entire amount of carbon dioxide contained in the natural gas, along with all heavier hydrocarbons. The bottoms product, a mixture of alkanes, is discharged into a pipeline after heating to ambient temperature, in the form of natural gas of low nitrogen content.

It is frequently desirable, however, to separate from a gaseous mixture several components having differing boiling ranges. For example, there is often interest in separating ethane and heavier hydrocarbons from natural gas in order to convert these components into more valuable products, such as ethylene, for example. The separation of a heavy fraction is also important where there is a demand for liquid gas. In addition, in the case of natural gases having a high nitrogen proportion, it is necessary in most instances to separate most of the nitrogen in order to obtain a particular caloric value for the end user.

To separate ethane and heavier hydrocarbons, as well as nitrogen, from natural gas, separate processes have heretofore been utilized; however, this is unsatisfactory, since the natural gas must be cooled down twice from the ambient temperature to the required low temperature levels.

SUMMARY OF THE INVENTION

An object of the invention is to provide a process and apparatus of the type mentioned above which is designed so that the separation of a light fraction and a heavy fraction from a gaseous mixture is conducted in an interrelated process. A particular object is to provide such an interrelated system for the separation of natural gas into several desired products.

Upon further study of the specification and appended claims, further object and advantages of this invention will become apparent to those skilled in the art.

To obtain these objects, there is provided a system wherein the gaseous mixture is separated in a first rectifying column into a head product and a bottom product; the bottom product, after heat exchange with the gaseous mixture, is expanded into a second rectifying column; and a further fractionation is carried out in a second rectifying column into a top product containing lower-boiling components and into a sump product containing higher-boiling components.

Thus, a system is provided by the present invention making it possible to separate simultaneously light and heavy components from a gaseous mixture. One important feature resides in that, besides the conventional fractionation of the head product of the first rectifying column, which can be conducted by means of a further rectification as described, for example, in DAS No. 2,122,707, the bottoms product of the first rectifying column is likewise further fractionated without heating this bottoms products first up to ambient temperature. Thereby, there are saved initial investment costs for additional heat-exchange surfaces, which would otherwise be required for two separate fractionation processes. Also, the process does away with the exergonic losses associated with such additional heat-exchange steps.

In a preferred embodiment of the invention, the compressed bottoms product of the first rectifying column is heated against the gaseous mixture to such an extent that partial vaporization occurs. This affords the advantage that the vaporized proportion of the bottoms product can be engine-expanded in an expansion engine e.g., a turbine. The thus-obtained energy can be utilized, directly or indirectly, for example, within the process for the compression of the feed gas.

In this manner of operation, it is especially advantageous to conduct the engine expansion into the liquid-vapor region and to utilize the thus-formed liquid as reflux for the second rectifying column. This procedure is recommended, in particular, if the bottoms product of the first rectifying column contains predominantly components which are to be separated overhead in the second rectifying column. Thus, for example, in the fractionation of natural gas, the bottoms product of the first rectifying column will contain methane as the primary component and additionally heavier hydrocarbons in a quantity of, for example, 5-25% by volume. The methane concentration will be so increased in the gaseous fraction obtained during the partial vaporization, that the liquid formed during engine expansion can be introduced in many instances as reflux liquid to the head of the second rectifying column without contaminating the head product with an undesirable amount of higher-boiling components. The gas not liquefied during the engine expansion can, in such cases, either be fed together with the thus-formed liquid to the head of the second rectifying column, from which the gas is then discharged directly, or the gas can be maintained apart from the second rectifying column.

In contrast thereto, if the top product of the second rectifying column does not attain the desired purity during the above-described procedure, additional measures can be used to obtain the desired purity, such as, for example, a head condenser operated with an external refrigerant or the introduction of further reflux liquid.

In some cases it may also prove advantageous to effect the engine expansion to a pressure below the pressure of the second rectifying column. This can be suitable, for example, if a specific power output of the expansion engine is desired, or if in this way a certain desired amount of reflux liquid can be formed. Before introducing the expanded fraction into the rectifying column, a phase separation is suitably conducted in such a mode of operation, whereafter the thus-obtained liquid is compressed to the pressure of the second rectifying column by means of an interposed pump, while the phase which has remained in the gaseous state can be discharged separately from the plant.

The proportion not vaporized during the heating of the bottoms product of the first rectifying column can be fed directly into the second rectifying column after expansion at a suitable location dependent on the composition of this fraction and the equilibrium curve in the second rectifying column. In an advantageous embodiment of the process, this fraction is partially vaporized prior to being fed into the second rectifying column, in order to improve the rectification conditions.

Insofar as components are contained in the gaseous mixture which, upon cooling to the temperatures of the rectification, lead to the precipitation of solids in the heat exchangers or in the rectifying column, these components must be separated after their condensation. In this connection, it has proven to be advantageous to introduce this condensate, which corresponding to the respective equilibrium conditions also contains minor amounts of lower-boiling components, into the second rectifying column at a suitable place for purposes of further processing.

Generally speaking, the process of this invention is applicable to the fractionation of gaseous mixtures containing besides methane and heavier hydrocarbons, lighter components like nitrogen, carbon monoxide or helium.

An apparatus for conducting the process of this invention comprises as the essential features two rectifying columns, a liquid pump connected to the bottom of the first rectifying column, a heat exchanger to heat the compressed bottoms product, as well as means for expansion of the compressed bottoms product into the second rectifying column. Insofar as a partial vaporization takes place during the heating of the bottoms product of the first rectifying column, the apparatus also advantageously contains a separator connected downstream of the heat exchanger, as well as advantageously an expansion engine to expand the gaseous fraction obtained in the separator. Moreover, it is expedient in many instances to provide a heat exchanger for the raw gaseous mixture, in order to precool same and condense out higher boiling substances. A phase separator is connected to the precooling heat exchanger, this separator comprising a condensate conduit leading to the second rectifying column and a conduit for discharging the gaseous fraction leading to the first rectifying column.

BRIEF DESCRIPTION OF THE FIGURE

The attached FIGURE is a schematic flowsheet of a preferred embodiment of the invention.

DETAILED DESCRIPTION OF FIGURE

Referring to the FIGURE, it is directed to a process for the separation of nitrogen and for obtaining a fraction of ethane and heavier hydrocarbons from a natural gas having the following composition:

| | |
|---|---|
| $N_2$ | 9.06% by volume |
| $CH_4$ | 75.37% by volume |
| $C_2H_6$ | 6.77% by volume |
| $C_3H_8$ | 4.76% by volume |
| $C_{4+}$ | 4.04% by volume |

This gaseous mixture is compressed in compressor 1 to 50 bar and thereafter, via conduit 2, cooled in heat exchanger 3 against cold product streams 22, 28, 29 and a precooling cycle 4 to a temperature of about 250° K. The components condensed during precooling are separated in separator 5 and expanded into the rectifying column 8 via conduit 6 and throttle valve 7 to a pressure of about 10 bar. The main portion, approximately 95%, of the original gaseous mixture is introduced from separator 5 via conduit 9 into the heat exchanger 10 wherein additional cooling takes place, and is then conducted through the heat exchanger 11 into the bottom of the rectifying column 12. Finally, this fraction is cooled again in heat exchanger 13 against cold product streams and, after expansion in throttle valve 14, fed into the rectifying column 12. The rectifying column 12 is operated under such conditions that there are produced a bottoms fraction largely free of nitrogen and a head fraction containing only nitrogen (37.70% by volume and methane (62.30% by volume). The bottoms product withdrawn via conduit 15 has the following composition:

| | |
|---|---|
| $N_2$ | 2.37% by volume |
| $CH_4$ | 78.43% by volume |
| $C_2H_6$ | 8.35% by volume |
| $C_3H_8$ | 5.87% by volume |
| $C_{4+}$ | 4.98% by volume |

This fraction is compressed in the liquid pump 16 to about 40 bar, and then heated in heat exchanger 10 to about 200° K. The bottoms product is generally compressed as much as possible thermodynamically, i.e. to such an extent that there is still a temperature gradient at the warm end of the heat exchanger 10 between the bottom product in conduit 15 and the raw gas in conduit 9. The components of the bottoms product revaporized in heat exchanger 10 are separated in separator 17 and fed via conduit 18 to an expansion turbine 19 wherein expansion is effected to the pressure of the rectifying column 8. The liquid withdrawn via conduit 20 from separator 17 is expanded in valve 21 and, after partial revaporization in heat exchanger 10, introduced into the rectifying column 8. From the rectifying column 8, a top product is discharged by way of conduit 22 having the following composition:

| | |
|---|---|
| $N_2$ | 2.88% by volume |
| $CH_4$ | 94.99% by volume |
| $C_2H_6$ | 2.02% by volume |
| $C_3H_8$ | 0.11% by volume |

This top product is rewarmed in heat exchangers 13, 10, and 3, releasing its refrigerant values, and introduced, for example, into a pipeline. Insofar as the discharge pressure is not predetermined by the pressure of the rectifying column 8, a compression of the top product is additionally carried out, if desired, which is not shown in the FIGURE.

The separated $C_{2+}$ fraction withdrawn from the sump of rectifying column 8 has the following composition:

| | |
|---|---|
| $CH_4$ | 1.00% by volume |
| $C_2H_6$ | 37.89% by volume |
| $C_3H_8$ | 32.83% by volume |
| $C_{4+}$ | 28.28% by volume |

To limit the methane content in the sump product of rectifying column 8, the sump is heated at 24 by partial streams from the raw gas and/or by circulating an external refrigerant cycle.

The purity of the head product of the rectifying column 12 is attained by means of a head condenser 25 operated with cycle gas. The head product, withdrawn via conduit 26, is fractionated in a further rectifying stage 27 (not shown in detail in the FIGURE) into a nitrogen fraction containing merely 2% by volume of methane, and into a methane fraction, containing 11.59% by volume of nitrogen. These fractions are withdrawn via conduits 28 and 29 and, after heating in heat exchangers 13, 10, and 3, are discharged from the plant.

In the above-described example, from natural gas fed in an amount of 189,818 Nm$^3$ per hour, 27,125 Nm$^3$ of a $C_{2+}$ fraction is withdrawn via conduit 23; in addition, 10,798 Nm$^3$ of nitrogen is obtained in conduit 28 and 25,105 Nm$^3$ of methane-enriched gas is obtained via conduit 22 at the head of rectifying column 8.

In case of an upset or shutdown of the nitrogen-methane fractionation process in the rectifying stages 12 and 27, respectively, these parts of the plant can be bypassed by the use of conduit 30 after opening valve 31, so that the process of producing the heavy fraction in the rectifying column 8 can be continued.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the separation of nitrogen and ethane from a natural gas mixture containing nitrogen and ethane, wherein a fraction containing all the nitrogen, and a fraction containing substantially all the ethane, are separated from the natural gas by rectifying under superatmospheric pressure, the natural gas being fractionated in a first rectifying column into a head product substantially freed of at least the ethane, and containing methane and nitrogen, and into a bottoms product containing methane and substantially all of the ethane from the natural gas, and substantially freed of nitrogen, the improvement comprising the steps of:
   compressing the liquids bottom product of the first rectifying column;
   passing the resultant compressed bottoms product through an indirect heat exchange with the natural gas for heating the compressed bottoms product;
   expanding the resultant heated compressed bottoms product and passing it into a second rectifying column;
   fractionating the expanded bottoms product in said second rectifying column to form a top product containing methane and a sump product containing ethane; and
   passing the head product from the first rectifying column to a separation unit for separating nitrogen from methane.

2. In a process for the rectification of a raw gaseous mixture under superatmospheric pressure, the raw gaseous mixture containing at least three components, wherein the gaseous mixture is fractionated in a first rectifying column into a head product freed of at least one higher-boiling component, and into a bottoms product substantially freed of at least one lower boiling component, the improvement comprising the steps of:
   precooling said raw gas before fractionation in the first rectifying column to at least partially condense the higher boiling components, separating resultant higher boiling condensate from the remaining gaseous fraction and introducing said higher boiling condensate into a second rectifying column;
   compressing the liquids bottom product from the first rectifying column;
   passing the resultant compressed liquids bottom product through an indirect heat exchange with the raw gaseous mixture;
   expanding resultant heated compressed bottoms product and passing it into the second rectifying column;
   fractionating the expanded bottoms product in said second rectifying column to form a top product containing lower-boiling components, and a sump product containing the higher-boiling components.

3. A process according to claim 2, further comprising at least partially vaporizing the compressed heated bottoms product of the first rectifying column, engine-expanding resultant vaporized bottom product fraction, and introducing resultant engine expanded fraction at least in part into the second rectifying column.

4. A process according to claim 3, wherein said gaseous mixture comprises natural gas, and wherein liquid is formed during said engine expansion step, and further comprising introducing said liquid as reflux into the head of the second rectifying column.

5. A process according to claim 3 further comprising passing the at least partially vaporized bottoms product into a phase separator to recover a vaporized bottoms product fraction and a liquid bottoms product fraction; at least partially vaporizing said liquid bottoms fraction; and introducing resultant at least partially vaporized liquid bottom product fraction into the second rectifying column.

6. A process according to claim 4, wherein said engine expansion is conducted to a pressure below the pressure of the second rectifying column to obtain a liquid, and further comprising recompressing the thus-obtained liquid to the pressure of the second rectifying column prior to introducing said liquid into the second rectifying column.

7. An apparatus for conducting a process for the rectification of a raw gaseous mixture under superatmospheric pressure as in claim 12, comprising:
   a first rectifying column (12) for fractionating the raw gaseous mixture;
   a liquid pump (16) connected to the bottom of said first rectifying column (12) for receiving and for compressing the bottoms product from said first rectifying column (12)
   heat exchange means (10) connected to said liquid pump (16) for passing the compressed bottoms product therethrough;
   separating means (17) connected to said heat exchange means (10);
   expanding means (19, 21) connected to said separating means for expanding the compressed bottoms product; and
   a second rectifying column (8) connected to said expanding means (19, 21) for receiving said expanded bottoms product for fractionation therein.

8. An apparatus according to claim 7 wherein said expanding means comprises an expansion engine (19) for the expansion of a gaseous fraction from the separating means (17).

9. An apparatus according to claim 7, further comprising precooling means (3) for the raw gaseous mixture, another separating means (5) connected downstream of said precooling means (3), said separating means (5) comprising a conduit (6) leading to the second rectifying column (8) for the introduction of condensate, and a conduit (9) leading to the first rectifying column (12) for the introduction of a gaseous fraction.

* * * * *